United States Patent [19]

Cole et al.

[11] 4,393,079

[45] Jul. 12, 1983

[54] PHARMACEUTICAL COMPOSITIONS

[75] Inventors: William G. Cole, Twickenham; Alexander C. Goudie, Harlow; Carl J. Rose, London, all of England

[73] Assignee: Beecham Group Limited, United Kingdom

[21] Appl. No.: 750,684

[22] Filed: Dec. 15, 1976

Related U.S. Application Data

[62] Division of Ser. No. 599,638, Jun. 20, 1975, Pat. No. 4,062,978.

[30] Foreign Application Priority Data

Jul. 4, 1974 [GB] United Kingdom ............... 29651/74

[51] Int. Cl.³ ..................... A61K 31/12; C07C 49/248
[52] U.S. Cl. .................................... 424/331; 564/328; 564/430; 424/311; 424/330; 424/337; 424/340; 424/341; 424/346; 424/347; 424/348; 424/343; 568/29; 568/30; 568/31; 568/306; 568/332; 568/333; 568/637; 568/636; 568/639; 568/638; 568/42; 568/43; 568/329; 568/330; 568/807; 568/808; 568/28; 568/32; 568/33; 568/44
[58] Field of Search ......................... 424/331; 260/591
[56] References Cited

U.S. PATENT DOCUMENTS 3,924,002 12/1975 Duennenberger et al. ......... 424/331
3,931,302 1/1976 Allais et al. ........................ 260/591
3,950,427 4/1976 Engel et al. ........................ 424/331

Primary Examiner—James H. Reamer
Attorney, Agent, or Firm—Jacobs & Jacobs

[57] ABSTRACT

Anti-inflammatory compositions are prepared which comprise a therapeutically effective amount of a compound of the formula

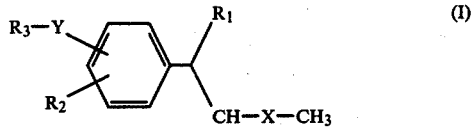

wherein X is CO or CHOH; Y is CO; the dotted line represents a double bond which is present or absent; $R_1$ is hydrogen or methyl; $R_2$ is hydrogen, fluorine, chlorine, bromine, methyl, trifluoromethyl, methoxyl, hydroxyl, acetoxyl, nitro or amino; $R_3$ is alkyl of 3 to 8 carbon atoms, cycloalkyl of 3 to 8 carbon atoms, alkenyl of 3 to 8 carbon atoms, cycloalkenyl of 5 to 8 carbon atoms or phenyl unsubstituted or substituted by 1 or 2 substituents selected from the group consisting of fluorine, chlorine, bromine, methyl, ethyl, methoxyl, ethoxyl, benzyloyl, hydroxyl, acetoxyl, trifluoromethyl, nitro, amino, acetyl, methylthiol, methylsulphonyl, methylamino and dimethylamino. Compounds of formula I above are also novel.

14 Claims, No Drawings

PHARMACEUTICAL COMPOSITIONS

CROSS-REFERENCE

This is a division of Ser. No. 599,638 filed June 20, 1975 now U.S. Pat. No. 4,062,978.

The present invention relates to pharmaceutical compositions useful for the treatment of inflammation, to the pharmacologically active aryl compounds for use in such compositions and to processes for the preparation of such aryl compounds.

A very large number of arylacetic and arylpropionic acids have been prepared in the search for non-steroidal anti-inflammatory agents. Many of these acids have been shown to possess excellent activity but almost all suffer from the disadvantage of being extremely irritant to the gastro-intestinal tract. An object of this invention is to provide anti-inflammatory agents which are of comparable effectiveness to the presently clinically available arylacetic and arylpropionic acid anti-inflammatory agents but which have a lower irritancy to the gastro-intestinal tract especially when taken orally.

We have now discovered that a group of derivatives of certain arylbutanes and arylpentanes possess potent anti-inflammatory activity but do not irritate the gastro-intestinal tract to any major extent at the therapeutic dose when administered orally.

Accordingly, the present invention provides a pharmaceutical composition which comprises in association a pharmaceutically acceptable carrier and a compound of the formula (I):

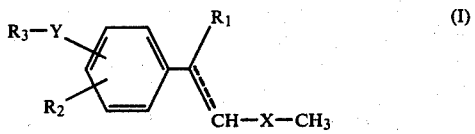

wherein:

X is a CO or CHOH group; Y is a CO group, an oxygen atom or a bond; the dotted line represents a double bond which is optionally present when Y is an oxygen atom or a bond; $R_1$ is a hydrogen atom or a methyl group; $R_2$ is a hydrogen, fluorine, chlorine or bromine atom or a methyl, trifluoromethyl, methoxyl, hydroxyl, acetoxyl, nitro or amino group; $R_3$ is a $C_{3-8}$ alkyl, $C_{3-8}$ cycloalkyl, $C_{3-8}$ alkenyl, or a $C_{5-8}$ cycloalkenyl group, a phenyl group, a phenyl group substituted by one or two groups selected from fluorine, chlorine, or bromine atoms or methyl, ethyl, methoxyl, ethoxyl, benzyloxyl, hydroxyl, acetoxyl, trifluoromethyl, nitro, amino, acetyl, methylthiol, methylsulphonyl, methylamino or dimethylamino groups.

When $R_3$ is an alkyl group, suitable compounds of the formula (I) include those wherein $R_1$ is a n-, sec-, iso- or tert- butyl group, or a straight or branched chain pentyl, hexyl, heptyl or octyl group.

When $R_3$ is a cycloalkyl group, suitable compounds of the formula (I) include those wherein $R_3$ is a cyclopropyl, cyclopentyl or cyclohexyl group.

When $R_3$ is an alkenyl group, suitable compounds of the formula (I) include those wherein $R_3$ is an allyl or but-2-enyl group.

When $R_3$ is a cycloalkenyl group, suitable compounds of the formula (I) include those wherein $R_3$ is the cyclopent-1-enyl or cyclohex-1-enyl group.

When $R_3$ is an aromatic group, suitable compounds of the formula (I) include those wherein $R_3$ is a phenyl, 2-fluorophenyl, 3-fluorophenyl, 4-fluorophenyl, 2-chlorophenyl, 2-bromophenyl, 4-chlorophenyl, 4-bromophenyl, 2,4-dichlorophenyl, 3-methylphenyl, 4-methoxylphenyl, 3-trifluoromethylphenyl, 4-nitrophenyl, 2,4-difluorophenyl, 2-fluoro-4-bromophenyl, 2-chloro-4-fluorophenyl, 4-methylthiolphenyl, 4-methylsulphonylphenyl or like group.

It is preferred in the compounds of the formula (I) as hereinbefore defined that X is a CO group, likewise that Y is a CO group or a bond, and that Y joins the $R_2$ substituted phenyl ring in the 3- or 4- position. It is also preferred that the phenyl substituents are selected from hydrogen, fluorine and chlorine atoms, or methyl, trifluoromethyl or methoxyl groups. Most suitably the phenyl substituents are hydrogen, fluorine or chlorine atoms.

One especially suitable group of di-aryl compounds of formula (I) are those of formula (II):

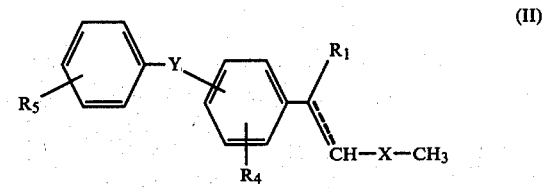

wherein $R_1$, X, Y and the dotted line are as defined in formula (I), and $R_4$ and $R_5$ are independently hydrogen, fluorine, chlorine or bromine atoms, or methyl, trifluoromethyl or methoxyl groups.

In formula (II) it is preferred that Y is a CO group or a bond, and joins the $R_4$ substituted phenyl ring at the 3- or 4- position. When Y is a bond, X is preferably a CO group.

Most suitably in formula (II), $R_4$ and $R_5$ are independently hydrogen, fluorine or chlorine atoms.

Within the group of compounds of formula (II) there are two sub-groups of particular interest, namely those of formula (III) and formula (IV):

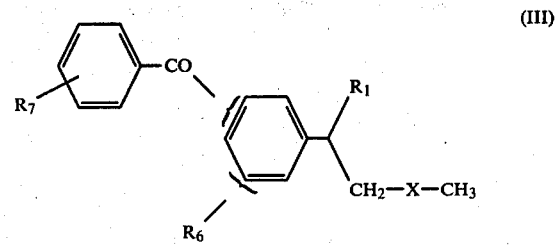

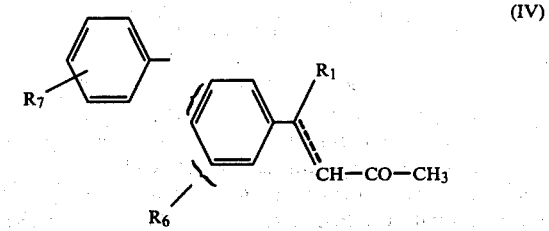

wherein $R_1$, X and the dotted line are as in formula (I), and $R_6$ and $R_7$ are independently hydrogen, fluorine or chlorine atoms.

Preferred compounds of the formula (III) include those of formula (V):

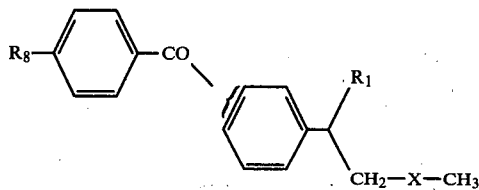

wherein $R_1$ and X are as in formula (I) and $R_8$ is a hydrogen, fluorine or chlorine atom. In formula (V) most suitably $R_8$ is a hydrogen or fluorine atom.

Preferred compounds of the formula (IV) include those of the formula (VI):

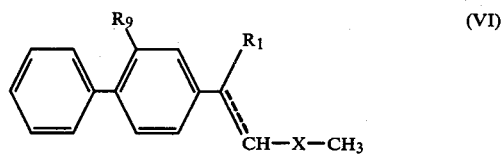

wherein $R_1$, X and the dotted line are as in formula (I) and $R_9$ is a hydrogen, fluorine or chlorine atom. In formula (VI) most suitably X is a CO group and $R_9$ is a hydrogen or fluorine atom.

One especially suitable group of mono-aryl compounds are those of the formula (VII):

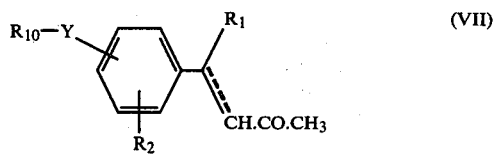

wherein $R_1$, $R_2$ and the dotted line are as in formula (I), and $R_{10}$ is a cyclopentyl, cyclohexyl, cyclohexenyl, straight or branched butyl, pentyl, hexyl, allyl or butenyl group.

Included within the compounds of formula (VII) are those of the formula (VIII):

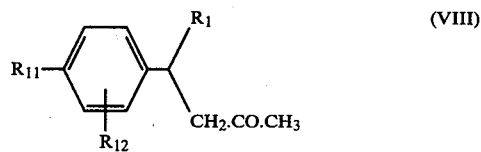

wherein $R_{11}$ is a cyclopentyl, cyclohexyl, cyclohexenyl, allyl, butenyl or straight or branched butyl, pentyl, or hexyl group and $R_{12}$ is a hydrogen, fluorine or chlorine atom.

The compositions of the invention may be in the form of an orally or parenterally administrable form and may be in the form of a unit dose or multi dose presentation. Suitable oral dosage forms include capsules, tablets, reconstitutable powders, sachets, syrups or any other conventional oral dosage form used for the administration of anti-inflammatory medicaments. Suitable parenteral dosage forms including suppositories, ointments for applying to skin and injectable preparations. Such dosage forms may contain one or more binders, diluents, disintegrants, buffers, colours, flavours, preservatives and the like in the manner understood by chemists or pharmacists skilled in the preparation of pharmaceutical formulations.

Preferred dosage forms include tablets and capsules. Suitable unit dosage formulations normally contain from 5 mgs. to 1000 mgs. of active ingredient and usually from 10 mgs. to 600 mgs. for example, from 20 mgs. to 400 mgs. of active ingredient.

The usual daily dosage required will depend upon the nature and severity of the inflammation to be corrected but a 70 kg. adult will normally be administered from 10 mgs. to 3000 mgs. of active material per day. More frequently, a daily dose of 20 mgs. to 2000 mgs. will be used. Normally the daily dosage will be given as divided doses, for example, from 2 to 8 administrations per day.

The invention further provides a method of treatment of inflammation in humans and animals which comprises the administration to the host of the inflammation of an effective amount of a compound of the formula (I).

Normally the compound of the formula (I) will be administered in the form of a pharmaceutical composition of the invention, as hereinbefore defined.

The compounds of the formula (I) are believed to be novel with the exception of the following compounds:

| | |
|---|---|
| 4-(3-Benzoylphenyl)butan-2-one | Ref. 1 |
| 4-(4-Benzoylphenyl)butan-2-one | Ref. 2 |
| 4-(4-Benzoylphenyl)-2-hydroxy-butane | Ref. 2 |
| 4-(4-Biphenylyl)but-3-en-2-one | Ref. 3 |
| 4-(4-Biphenylyl)butan-2-one | Ref. 3 |

References:
1. Prepared and described in German Offenlegungsschrift 2243444 as a useful intermediate in the synthesis of anti-inflammatory butyric acid derivatives.
2. P. T. Lansbury and J. O. Peterson, J. Amer. Chem. Soc., 1963, 85, 2236.
3. Cromwell and Cahoy J.A.C.S., 80, 1958, 5524-7. This is a synthetic disclosure of the compound—no pharmaceutical activity of any kind is mentioned in the paper.

Thus it will be apparent that within formula (I) there are several groups of novel compounds which form an important part of this invention. They include the following groups.

Compounds of the formula (I) as hereinbefore defined, except that $R_1$ must be a methyl group: when $R_3Y$ is a 4- phenyl group, $R_2$ is a hydrogen atom and X is a CO group; when $R_3Y$ is a 4- benzoyl group and $R_2$ is a hydrogen atom; and also when $R_3Y$ is a 3- benzoyl group, $R_2$ is a hydrogen atom and X is a CO group.

Mono-aryl compounds of the formula (VII) and (VIII) as hereinbefore defined.

Di-aryl compounds within the formula (II) as hereinbefore defined, of the formulae:

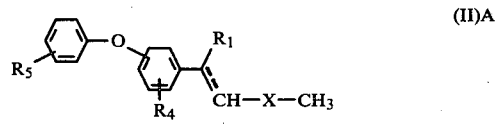

-continued

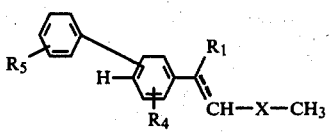 (II)B

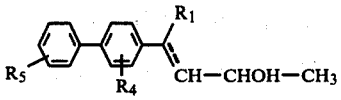 (II)C

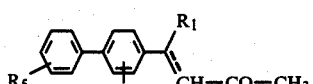 (II)D

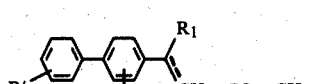 (II)E

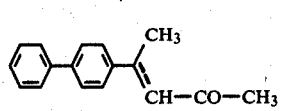 (II)F

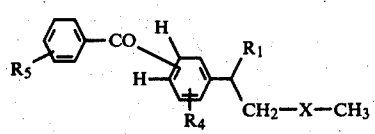 (II)G

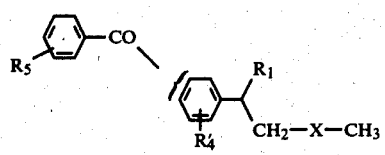 (II)H

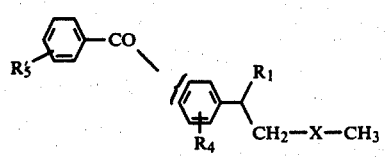 (II)J

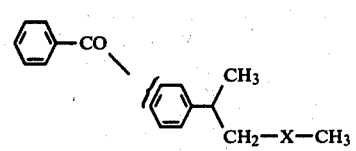 (II)K

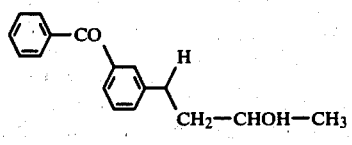 (II)L

In formulae (II)A-K, $R_1$, $R_4$, $R_5$, X, Y and the dotted line have the same meaning as in formulae (I) and (II). $R_4'$ and $R_5'$ are independently fluorine, chlorine or bromine atoms, or methyl, trifluoromethyl or methoxyl groups.

In formulae (II)A-K, preferred values for $R_4$ and $R_5$ are independently hydrogen, fluorine or chlorine atoms, and for $R_4'$ and $R_5'$ independently fluorine or chlorine atoms.

It will be appreciated that the preferred novel compounds are those included within the preferred compounds for use in the pharmaceutical compositions as stated hereinbefore. Thus preferred groups of novel compounds include the following:

Compounds of formula (II)C, wherein $R_5$ is a hydrogen atom and $R_4$ is a 3-hydrogen, fluorine or chlorine atom (preferably a 3-hydrogen or fluorine atom).

Compounds of the formula (II)D, wherein $R_5$ is a hydrogen atom and $R_4'$ is a 3-fluorine or chlorine atom (preferably a 3-fluorine atom).

Compounds of the formula (II)F.

Compounds of the formula (II)J, wherein $R_5'$ is a 4-fluorine or chlorine atom (preferably a 4-fluorine atom) and $R_4$ is a hydrogen atom.

Compounds of the formulae (II)K and (II)L.

Where appropriate in these preferred compounds X is most suitably a CO group.

The novel compounds of the invention may be prepared by chemical techniques as indicated in the following Sections A-D. The preparation of the novel compounds of this invention by such processes form an important aspect of this invention.

Section A

Compounds of the formula (I) not possessing acylatable groups may be prepared by the methylation of the appropriate acyl halide thus:

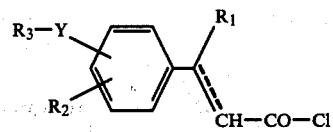

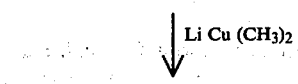

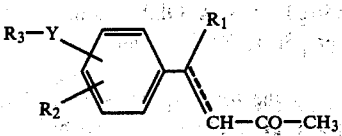

Section B

Compounds of formula (I) wherein Y is a carbonyl group may in general, be prepared by conventional Friedel-Craft acylation thus:

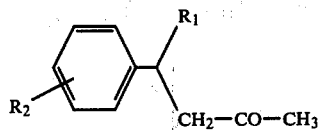

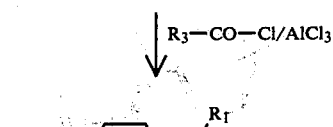

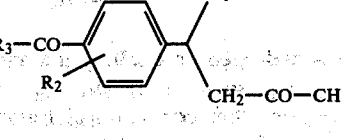

Suitable reaction conditions for such acylations include those obtainable from 'Friedel-Crafts and Related Reactions', edited by G. A. Olah, published by Interscience Publishers, New York, (1964).

Section C

Compounds of the formula (I) wherein Y is a bond or an oxygen atom may be prepared by alkylation using an unsaturated methyl ketone thus:

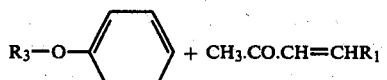

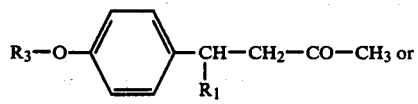

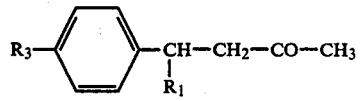

Suitable reaction conditions for such alkylations include those obtainable from 'Friedel-Crafts and Related Reactions', edited by G. A. Olah, published by Interscience Publishers, New York, (1964).

Section D

Compounds of the formula (I) wherein Y is an oxygen atom may in general be prepared by conventional methods of alkylation or arylation thus:

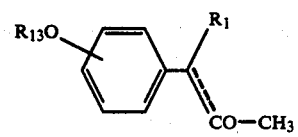

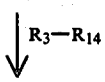

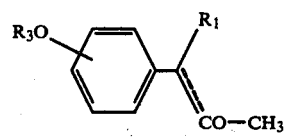

wherein $R_{13}$ is hydrogen or a salting ion and $R_{14}$ is a displaceable group such as I, Br, Cl, $OSO_2CH_3$, $OSO_2C_6H_4CH_3$ or other conventional leaving group. When $R_3$ is an aryl group, a catalyst such as copper powder or copper oxide is normally employed.

A variant of this process will involve the reaction of a compound $R_3$-$R_{13}$ with a compound such as:

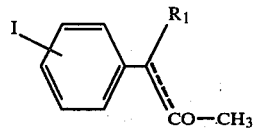

or the like in the presence of a copper or copper oxide catalyst or the like.

After the preparation of a compound of the formula (I) by any of the aforesaid methods, that compound of the formula (I) may then be converted into another compound of the formula (I) by conventional methods. For example compounds wherein Y is a CO group may generally be reduced to the corresponding compounds wherein Y is a bond. Similarly compounds wherein X is a CO group may generally be reduced to the corresponding compounds wherein X is a CHOH group.

The following Examples illustrate the preparation and pharmacological properties of representative compounds of the formula (I).

EXAMPLE 1

4-(p-Benzoylphenyl)-2-butanone

To a vigorously stirred solution of aluminum chloride (0.2 mole) in methylene chloride (250 ml.) was added in turn benzylacetone (0.1 mole) and then benzoyl chloride (0.1 mole), the reaction mixture being kept at 0° C. throughout. The resulting solution was refluxed overnight, cooled and poured onto a mixture of ice and concentrated hydrochloric acid. The organic phase was washed with dilute sodium bicarbonate solution, dried and concentrated. The crude product was purified by distillation, b.p. 200–220 (2 mm), followed by crystallisation from benzene-petroleum ether, to give the pure diketone as colourless needles, m.p. 36°–7° C. (lit. 35°–7° C., reference 2).

EXAMPLE 2

4-(p-Benzoylphenyl)-2-butanol

A mixture of 4-(p-benzoylphenyl)-2-butanone (2.5 g.) and lithium aluminum hydride (0.38 g.) was stirred overnight at room temperature in dry tetrahydrofuran (200 ml). The tetrahydrofuran was then removed, replaced with ether, and successive additions of cold water (1 ml), 10% aqueous sodium hydroxide (1 ml) and cold water (3 ml) were made. The mixture was then filtered, the organic layer separated, washed with brine, dried and concentrated to afford an oily diol.

A mixture of the above diol (1 g.) and manganese dioxide (5 g.) was stirred for seven hours at room temperature in benzene, filtered and then concentrated to give 4-(p-benzoylphenyl)-2-butanol, identical to the compound made by the alternative method given in reference 3 (loc. cit.).

EXAMPLE 3

4-(p-Cyclohexylphenyl)-2-butanone

To a stirred solution of aluminium chloride (0.15 mole) in cyclohexylbenzene (0.5 mole) at 10°–15° C. was added dropwise methyl vinyl ketone. The resulting mixture was left overnight at room temperature and worked up as above. The crude ketone was purified by distillation, b.p. 150–60 (2 mm), followed by column chromatography using silica as support and petrol/ethyl acetate as eluants.

EXAMPLE 4

4-(p-Tertiary butylphenyl)-2-butanone

As Example 2 except that tertiary butyl benzene was used instead of cyclohexyl benzene. The crude product was purified by distillation, b.p. 120–40 (1 mm), followed by chromatography as in Example 3.

EXAMPLE 5

4-(p-Cyclohexoylphenyl)-2-butanone

As in Example 1 except that cyclohexane carboxylic acid chloride was used instead of benzoyl chloride. The crude product was purified by distillation and re-crystallisation from petroleum ether m.p. 69.5°–70° C.

EXAMPLE 6

4-(p-Iso-butyrylphenyl)-2-pentanone

As in Example 1 except using 4-phenyl-2-pentanone instead of benzyl acetone, and iso butyryl chloride instead of benzoyl chloride b.p. 130–134 (0.4 mm).

EXAMPLE 7

4-[4-(p-Chlorobenzoyl)phenyl]-2-butanone

To a vigorously stirred solution of aluminum chloride (0.2 mole) in carbon disulphide (200 ml.) at 0° C. was added a mixture of benzylacetone (0.1 mole) and p-chlorobenzoyl chloride (0.1 mole) throughout 20 minutes. After a further hour at 0° C., the reaction was allowed to reach room temperature and left overnight. The supernatant carbon disulphide was decanted off and the crude, brown residual oil, was poured carefully onto a mixture of ice and concentrated hydrochloric acid. Work-up in the usual way afforded an oil, which, after trituration with acetone and re-crystallisation from benzene/60°–80° C. petrol, gave pure 4-[4-(p-chlorobenzoyl)phenyl]-2-butanone as colourless needles, m.pt. 91°-2° C.

EXAMPLE 8

4-[4-(p-Fluorobenzoyl)phenyl]-2-butanone

This was prepared in a similar manner to Example 7. Re-crystallisation from benzene/60°–80° C. petrol gave colourless needles of 4-[4-(p-fluorobenzoyl)-phenyl]-2-butanone, m.pt. 67°–8° C.

EXAMPLE 9

4-(p-Benzoylphenyl)-2-pentanone

This was prepared in a similar manner to Example 1 using 4-phenyl-2-pentanone instead of benzyl acetone. Distillation of the crude product gave pure 4-(p-benzoylphenyl)-2-pentanone, b.p. 174°–180° C. (0.1 mm).

EXAMPLE 10

4-(p-Isobutylphenyl)-2-pentanone 4-(p-isobutyrylphenyl)-2-pentanone (2 g.) was shaken in ethyl acetate (50 ml) with 10% pd/1 (200 mg) in the presence of hydrogen and one drop of perchloric acid. After the uptake of hydrogen had ceased, the solution was filtered, washed with aqueous sodium bicarbonate and evaporated, giving 4-(p-isobutylphenyl)-2-pentanone b.p. 109° C. (0.3 mm).

EXAMPLE 11

4-(p-Cyclohexylmethylphenyl)-2-butanone

In a similar manner was prepared 4-(p-cyclohexylmethylphenyl)-2-butanone from 4-(p-cyclohexoylphenyl)-2-butanone as an oil, ex column.

EXAMPLE 12

4-(p-Allyloxyphenyl)-2-butanone p-Hydroxy benzylacetone (1.5 g.), KOH (6 g.) and allyl bromide (1.2 g.) were stirred in ethanol (50 ml) overnight. Water was added and the mixture extracted with ether, which was evaporated to give the compound (1.6 g.) as an oil purified by column chromatography.

EXAMPLE 13

4-(m-Benzoylphenyl)-2-butanone

A mixture of 3-bromomethylbenzophenone (2.75 g.), acetylacetone (1 g.), potassium carbonate (1.4 g.) and ethanol (50 ml) was refluxed for 2 hours. The solvent was then evaporated and the residue extracted with ether. Distillation of the concentrated extracts gave 4-(m-benzoylphenyl)-2-butanone (1 g.), b.p. 220° C. (4 mm). [An alternative preparation of this compound appears in German Offenlegungsschrift 2243444].

EXAMPLE 14

4-(m-Phenoxyphenyl)-2-pentanone m-Phenoxyacetophenone (21 g.) was added to a solution of triethylphosphonoacetate (22 g.) and sodium hydride (2.4 g.) in dry dimethoxyethane (200 ml). The mixture was refluxed under nitrogen for ½ hour, poured onto water and extracted with ether, giving on distillation a pale yellow oil (28 g.).

IR: Carbonyl absorption at 1708 cm$^{-1}$.

The above oil (28 g.) in ethanol (100 ml) was shaken over hydrogen and platinum oxide (0.5 g.) until the uptake of hydrogen had ceased. Filtration and evaporation of the solvents yielded ethyl 3-(m-phenoxyphenyl)-butyrate (28 g.) as a colourless oil.

IR: Carbonyl absorption at 1730 cm$^{-1}$.

Hydrolysis of this oil (28 g.) in ethanol (100 ml) using 10% aqueous sodium hydroxide (200 ml) for 1 hour afforded 3-(m-phenoxyphenyl)-butyric acid (21.3 g.) as a pale yellow oil.

IR: Carbonyl absorption at 1700 cm$^{-1}$.

A solution of 3-(m-phenoxyphenyl)-butyryl chloride (1 g.) (from the corresponding acid (1 g.) using excess oxalyl chloride in benzene) in ether (20 ml) was added dropwise to a solution of dimethyl copper lithium at −70° C. under nitrogen (from methyl lithium (0.2 g.) and cuprous iodide (1 g.)) in ether (50 ml) and the mixture stirred a further 15 minutes at −70° C. Methanol was added to quench the reaction and the mixture was diluted with water, acidified and filtered through a pad of Kieselguhr. The ether layer was washed with sodium carbonate solution and with water, dried over anhydrous magnesium sulphate and evaporated to give a colourless oil. The product was purified by column chromatography to give 4-(m-phenoxyphenyl)-2-pentanone as a colourless oil.

IR: Carbonyl absorption at 1705 cm$^{-1}$

NMR: CH$_3$CO-: 3 proton singlet at 7.9$\tau$

CH₃—CH: 3 proton doublet at 8.7τ, J = 11 cps.

EXAMPLE 15

4-(4-Phenyl-phenyl)-2-pentanone

As Example 14 using 4-acetyl biphenyl as the starting material. 4-(p-phenyl-phenyl)-2-pentanone was obtained as a colourless solid, m.p. 67° C. from ethanol/pentane.

EXAMPLE 16

4-(3-Fluoro-4-phenyl-phenyl)-2-pentanone

As Example 14 using 3-fluoro-4-phenyl acetophenone as starting material. 4-(3-fluoro-4-phenyl-phenyl)-2-pentanone was obtained as a colourless solid, m.p. 85° C. from 80°-100° C. petroleum ether.

EXAMPLE 17

4-[-(p-Methoxybenzoyl)phenyl]-2-butanone

This was prepared in a similar manner to Example 7 except that the initial reaction product (13 g.) was dissolved in ethanol (250 ml) and treated successively with 40% aqueous sodium hydroxide (5 ml) and dimethyl sulphate (6.3 g.) and then left overnight. The ethanol was then removed and the crude product extracted into ether. Crystallisation of the product from ether afforded pure 4-[4-(p-Methoxybenzoyl)-phenyl]-2-butanone, m.p. 89°-91° C.

EXAMPLE 18

4-(3-Benzoyl-4-methoxyphenyl)-2-butanone

To a stirred mixture of 4-(4-methoxyphenyl)-2-butanone (15.4 g.), benzoyl chloride (13 g.) and methylene chloride (250 ml) at 0° C. was added portionwise aluminium chloride (23 g.) over a 20 minute period. The mixture was stirred a further 1 hour at room temperature and then poured onto ice and worked up in the usual way. Distillation of the product gave 4-(3-benzoyl-4-methoxyphenyl)-2-butanone (12 g.), b.p. 188°-192° C. (0.01 mm).

EXAMPLE 19

4-(4-Phenyl-phenyl)-but-3-en-2-one

The title compound was prepared according to the method of Cromwell and Cahoy J.A.C.S. 80, 1958, 5526. m.p. (lit.) 135° C.

EXAMPLE 20

4-(4-Phenyl-phenyl)-2-butanone

The title compound was also prepared by the method of Cromwell and Cahoy (loc. cit.). m.p. (lit.) 75°-77° C.

EXAMPLE 21

Pharmacological Activity

Four of the compounds prepared in the Examples were tested in the Carrageenin Rat Paw Oedema Test for anti-inflammatory activity.

The following results were obtained:

| Compound | Active Dose mg/kg p.o. |
| --- | --- |
| Example 15: 4-(4-Phenyl-phenyl)-2-pentanone | 33.3 |
| Example 16: 4-(3-Fluoro-4-phenyl-phenyl)-2-pentanone | 33.3 |
| Example 19: 4-(4-Phenyl-phenyl)-but-3-en-2-one | 30 |
| Example 20: 4-(4-Phenyl-phenyl)-2-butanone | 33.3 |

What is claimed is:

1. A pharmaceutical composition useful for the treatment of inflammation in humans and animals which comprises an anti-inflammatory amount of a compound of the formula

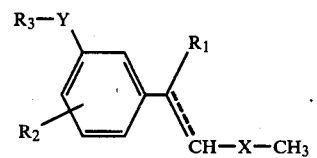

wherein
X is CO or CHOH;
Y is CO;
the dotted line represents a double bond which is present or absent;
$R_1$ is hydrogen or methyl;
$R_2$ is hydrogen, fluorine, chlorine, bromine, methyl, trifluoromethyl, methoxyl, hydroxyl or nitro; and
$R_3$ is phenyl unsubstituted or substituted by 1 or 2 substituents selected from the group consisting of fluorine, chlorine, bromine, methyl, ethyl, methoxyl, ethoxyl, hydroxyl, trifluoromethyl, nitro, methylthio or methylsulphonyl;
in combination with a pharmaceutically acceptable carrier.

2. A method of treating inflammation in humans and animals which comprises administering to a human or animal in need thereof an anti-inflammatory amount of a compound of the formula

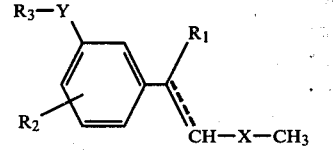

wherein
X is CO or CHOH;
Y is CO;
the dotted line represents a double bond which is present or absent;
$R_1$ is hydrogen or methyl;
$R_2$ is hydrogen, fluorine, chlorine, bromine, methyl, trifluoromethyl, methoxyl, hydroxyl or nitro; and
$R_3$ is phenyl unsubstituted or substituted by 1 or 2 substituents selected from the group consisting of fluorine, chlorine, bromine, methyl, ethyl, methoxyl, ethoxyl, hydroxyl, trifluoromethyl, nitro, methylthio or methylsulphonyl;
in combination with a pharmaceutically acceptable carrier.

3. A composition according to claim 1 wherein the compound is of the formula

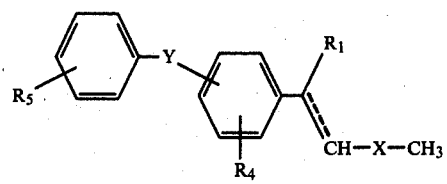

(II)

wherein X is CO or CHOH; Y is CO; the dotted line represents a double bond which is present or absent; $R_1$ is hydrogen or methyl; $R_4$ is hydrogen, fluorine, chlorine, bromine, methyl, trifluoromethyl or methoxyl; and $R_5$ is hydrogen, fluorine, chlorine, bromine, methyl, trifluoromethyl or methoxyl.

4. A composition according to claim 3 wherein Y is attached to the $R_4$ substituted phenyl ring in the 3- or 4-position.

5. A composition according to claim 4 wherein $R_4$ is hydrogen, fluorine or chlorine and $R_5$ is hydrogen, fluorine or chlorine.

6. A composition according to claim 1 wherein the compound is of the formula

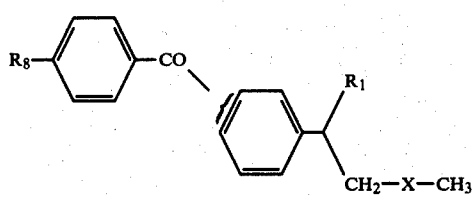

(V)

wherein X is CO or CHOH; $R_1$ is hydrogen or methyl and $R_8$ is hydrogen, fluorine or chlorine.

7. A composition according to claim 6 wherein the compound is 4-benzoyl-phenyl-2-pentanone.

8. A composition according to claim 6 in oral administration form.

9. A method according to claim 2 wherein the compound is of the formula

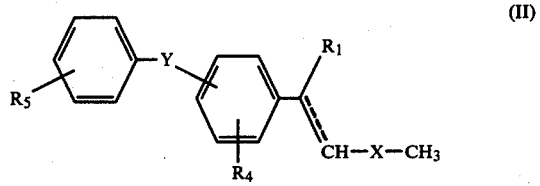

(II)

wherein X is CO or CHOH; Y is CO; the dotted line represents a double bond which is present or absent; $R_1$ is hydrogen or methyl; $R_4$ is hydrogen, fluorine, chlorine, bromine, methyl, trifluoromethyl or methoxyl; and $R_5$ is hydrogen, fluorine, chlorine, bromine, methyl, trifluoromethyl or methoxyl.

10. A method according to claim 9 wherein Y is attached to the $R_4$ substituted phenyl ring in the 3- or 4-position.

11. A method according to claim 10 wherein $R_4$ is hydrogen, fluorine or chlorine and $R_5$ is hydrogen, fluorine or chlorine.

12. A method according to claim 2 wherein the compound is of the formula

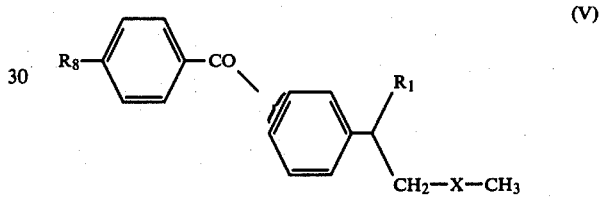

(V)

wherein X is CO or CHOH; $R_1$ is hydrogen or methyl and $R_8$ is hydrogen, fluorine or chlorine.

13. A method according to claim 12 wherein the compound is 4-benzoyl-phenyl-2-pentanone.

14. A method according to claim 12 wherein the administration is oral.

* * * * *